United States Patent [19]

Potter et al.

[11] 4,041,313

[45] Aug. 9, 1977

[54] EMITTANCE CALORIMETRIC METHOD

[75] Inventors: Roy F. Potter, San Diego; Donald L. Stierwalt, El Cajon, both of Calif.

[73] Assignee: The United States of America as represented by the Secretary of the Navy, Washington, D.C.

[21] Appl. No.: 628,261

[22] Filed: Nov. 3, 1975

[51] Int. Cl.² ........................................... G01N 21/22
[52] U.S. Cl. .................................. 250/341; 356/51; 356/201
[58] Field of Search ...................... 356/43, 45, 51, 75, 356/85, 201, 256; 73/190 R, 190 EW; 250/338, 340, 341, 351

[56] References Cited

U.S. PATENT DOCUMENTS

| | | | |
|---|---|---|---|
| 3,723,007 | 3/1973 | Leonard | 356/75 |
| 3,811,782 | 5/1974 | Kerr | 356/201 |
| 3,887,471 | 6/1975 | Stotlar | 250/338 |

OTHER PUBLICATIONS

Weil, *Journal of Applied Physics*, vol. 41, No. 7, June 1970, pp. 3012-3014.

*Primary Examiner*—F. L. Evans
*Attorney, Agent, or Firm*—R. S. Sciascia; G. J. Rubens; T. M. Phillips

[57] ABSTRACT

A precise measurement of the absorption of weakly absorbing optical material is measured by measuring the temperature rise of the sample when light of the wavelength of interest passes through it. The temperature rise is determined by measuring the emission from the sample due to phonon absorption processes. This emission is of a much longer wavelength than the wavelength of interest. The temperature rise is measured by measuring the rate of increase of the emitted radiation power from the sample at the longer wavelength.

8 Claims, 1 Drawing Figure

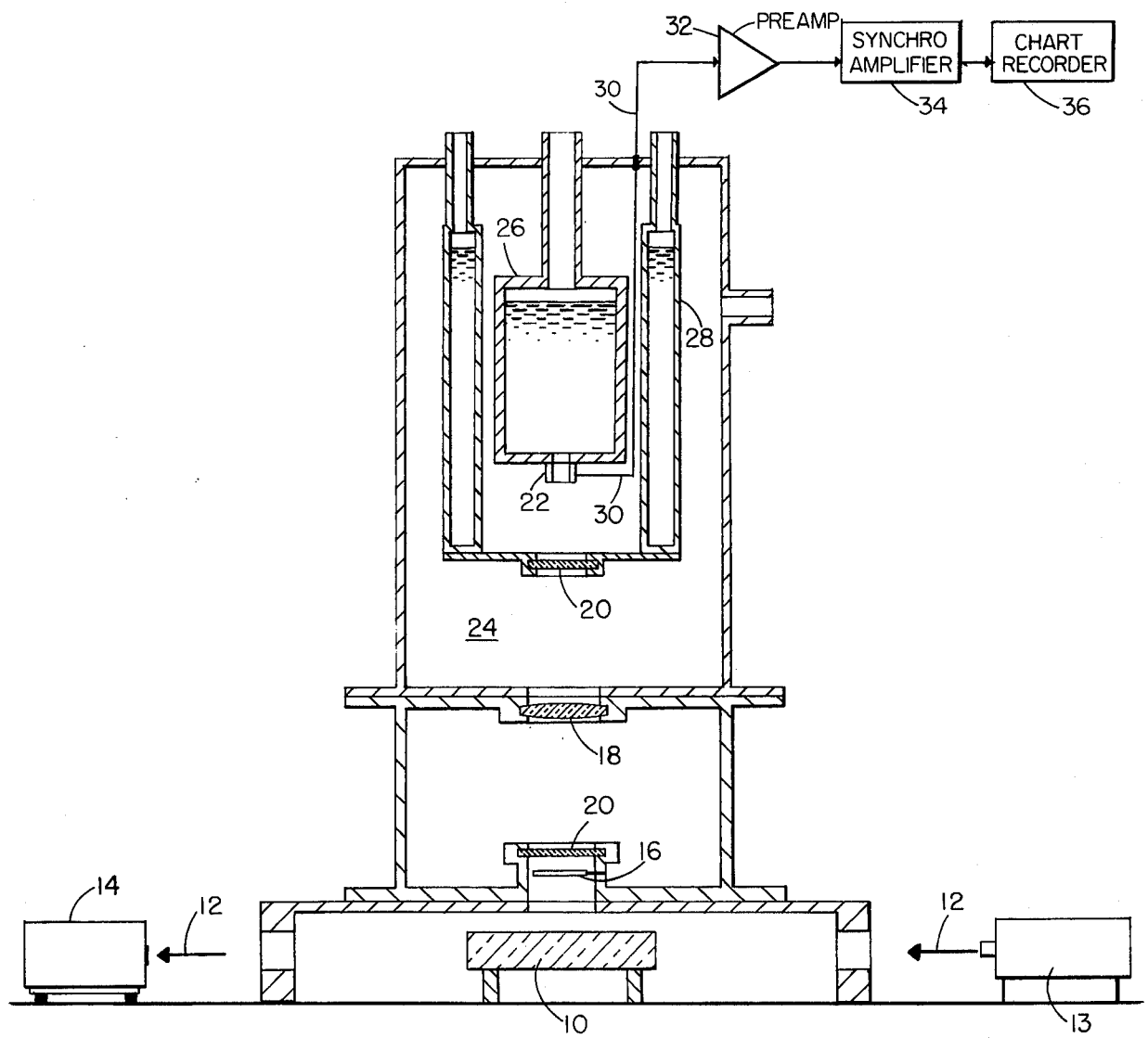

EMITTANCE CALORIMETRIC METHOD

BACKGROUND OF THE INVENTION

The development of high power lasers has put a premium on the development of window materials having absorption coefficients of the order of $10^{-3} cm^{-1}$ or lower for wavelengths corresponding to the lasers of interest. Heretofore measurements have been made by measuring the optical properties by conventional techniques at the wavelength of interest (i.e., transmittance, reflectance, and/or emittance). These techniques generally require extreme sensitivity and are limited to absorption coefficient-length products ($\alpha d$) of $10^{-2}$. Usually it is necessary to attach a thermocouple to the specimen in order to measure the rate of change of the change in temperature of the specimen. The sensitivity of thermocouples seriously limits the measurements of $\alpha d$ to the order of $10^{-3}$ and have additional disadvantages of responding to incident radiation and are difficult to attach to the specimen under test.

SUMMARY OF THE INVENTION

The present invention provides a convenient and precise means of measuring the absorption of weakly absorbing optical materials by utilizing the spectral emittance due to phonon absorption processes and measures the temperature rise by measuring the rate of increase of the emitted radiated power from the sample at appropriate wavelength bands.

OBJECTS OF THE INVENTION

Accordingly, an object of the invention is the provision of a rapid and accurate measurement in optical materials of ultra-low absorption not achieved with methods in present day usage.

Another object of the invention is to measure the absorption of weakly absorbing materials without the use of large samples in order to achieve a high level of sensitivity.

Still another object of the invention is to make measurements by applying laser energy to the specimen which will not affect the probe measurements because measurement is made at a wavelength different from the laser energy wavelength.

A further object is to provide a means of measuring the absorption of weakly absorbing optical materials that is more sensitive than heretofore known measuring techniques.

Other objects, advantages and novel features of the invention will become apparent from the following detailed description of the invention when considered in conjunction with the accompanying drawings wherein there is shown in the single FIGURE, an apparatus illustrating a means of carrying out the invention.

DESCRIPTION OF THE PREFERRED EMBODIMENTS

Referring now to the drawing wherein there is shown in the single FIGURE a specimen of optical material 10, as for example KCl, on which the absorption measurement is to be made. A laser beam shown as an arrow 12 from a source 13, which may be any of the well known laser sources, is passed through specimen 10 and terminated in a power meter 14. The passing of laser beam 12 through specimen 10 causes it to rise in temperature and radiate due to the phonon processes. The radiation from sample 10 is chopped by means of a chopper 16, which may be by way of example a tuning fork, and focused through an optical system 18 and filtered by means of filters 20 to an optical detector 22. Filters 20 should be of the type to block the laser wavelength and pass the wavelength of interest on which measurements are to be made. The long wavelength pass filter No. L18830-8 made by Optical Cooling Laboratory has been found to be satisfactory. Zinc doped Germanium, Antimony doped silicon or other detector sensitive in appropriate wavelength region available from Santa Barbara Research may be used as detector 22.

Detector 22 is maintained at a constant temperature by attaching it to the base of a container 26 filled with liquid Helium. A heat shield 28 filled with liquid Nitrogen is provided to prevent rapid evaporation of the liquid Helium. The output signal from detector 22 is fed through an electrical lead 30 to pre-amplifier 32 and synchronous amplifier 34 to a chart recorder 36.

Since solid state window materials have absorption that increases as the measuring wavelength is increased until wavelengths corresponding to the fundamental lattice modes are reached (phonon absorption processes account for this); i.e., the intrinsic absorption is many orders of magnitude greater than it is for pure materials at intermediate wavelengths. Optical materials useful for laser window applications have extremely low absorption for wavelengths at the laser wavelength $\lambda_L$ such that $$\lambda_{FE} < \lambda_L \text{ and is much less} << \lambda_R$$

where $\lambda_R$ is the fundamental lattice mode wavelength and $\lambda_{FE}$ is the fundamental edge wavelength below which the interband electronic transitions cause strong and intrinsic absorption. Since these materials emit more strongly at the longer wavelengths the radiation from specimen 12 is passed through filter 20 to allow only the longer wavelengths to pass to detector 22. Filter 20 also serves to filter out any radiations from the laser beam 12.

In operation, and by way of example in the apparatus shown with a field of view (fov) of 0.2 ster.
a sample emittance
$E = 0; 1 < \lambda < 30 \mu m$
$E = 0.7; 30 \mu m < \lambda < \infty$
filter transmittance $0 < 20 \mu m$
$0.5 > 20 \mu m$
$T_1 = 300° K$
lens transmits 60% and is $f:1$
and detector $NEP(H_z^{1/2}) = 10^{-12}$ watts $H_z^{1/2}$.

The detector will have a signal S of $5 \times 10^{-9}$ watts per degree temperature rise of the specimen as measured in the spectral band 30–40 $\mu$m. Thus the noise equivalent $\Delta T$ will be $NE\Delta T = S/NEP \approx 2 \times 10^{-4} K$, for a 1 Hertz bandwidth measurement.

With a 10-watt laser beam at 10.6 $\mu$m
and specimen 10 has $\alpha d = 5 \times 10^{-5}$
and specimen dimensions are $(0.5 \times 0.5 \times 0.5) cm^3$
and specimen 10 has properties of CdTe
a. Specific heat at 300° K 0.45 cal/grmK
b. Density 5.85 grms/cm$^3$ The power absorbed is $5 \times 10^{-4}$ watts $\approx 1.2 \times 10^{-4}$ cal/sec and the rate of change of $\Delta T$ recorded on chart recorder 36 is $\sim 3.6 \times 10^{-3}$ K/sec. The noise equivalent $\Delta T$ will be reached in less than 0.10 sec under the conditions described above.

The present invention thus provides a more sensitive rapid and accurate measurement in optical materials of ultra-low absorption. Also the laser energy does not affect the probe measurements because adequate wavelength filtering is provided.

In an alternative configuration a folded mirror arrangement could be used in place of the lens 18.

Obviously many modifications and variations of the present invention are possible in the light of the above teachings. It is therefore to be understood that within the scope of the appended claims the invention may be practiced otherwise than as specifically described.

What is claimed is:

1. A method of making a precise measurement of the absorption of weakly absorbing optical materials by measuring the temperature rise of the sample when light of the wavelength of interest passes through said sample, comprising the steps of:
   a. passing light of a first predetermined wavelength through a sample of the weakly absorbing material;
   b. measuring the rate of increase in power emitted by said sample at a second predetermined wavelength.

2. The method of claim 1 wherein said measuring step further comprises the step of filtering the emission radiated from said sample to allow only energy in the spectral region where the sample is a strong emitter.

3. The method of claim 2 wherein the first predetermined wavelength is in the spectrum of light emitted from a laser source.

4. The method of claim 3 wherein the second predetermined wavelength is in the infrared spectrum.

5. The method of claim 4 wherein said measuring step further includes the step of detecting the temperature rise of said sample by detecting the rate of increase in power emitted by the sample in the infrared spectral region.

6. A method of measuring the absorption of weakly absorbing optical materials the steps comprising:
   a. passing a light of a first predetermined wavelength through the sample to cause said sample to increase the amount of energy emitted due to a rise in temperature;
   b. focusing and filtering the emission of said sample to exclude all radiation other than the energy emitted at a second predetermined wavelength;
   c. measuring the rate of increase of the emitted radiation power from said sample at said second predetermined wavelength.

7. The method as recited in claim 6 wherein said first predetermined wavelength is in the spectral region of laser emittance.

8. The method as recited in claim 7 wherein said second predetermined wavelength is in the infrared spectral region.

* * * * *